(12) United States Patent
Takayama et al.

(10) Patent No.: US 7,867,965 B2
(45) Date of Patent: Jan. 11, 2011

(54) ALKALINE DETERGENT FOR AUTOMATIC ANALYZER, WASHING METHOD FOR AUTOMATIC ANALYZER, AND AUTOMATIC ANALYZER

(75) Inventors: Hiroko Takayama, Otawara (JP); Michiaki Takeuchi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1155 days.

(21) Appl. No.: 11/425,894

(22) Filed: Jun. 22, 2006

(65) Prior Publication Data

US 2006/0293200 A1    Dec. 28, 2006

(30) Foreign Application Priority Data

Jun. 23, 2005    (JP) .............................. 2005-183458

(51) Int. Cl.
*C11D 17/00* (2006.01)
(52) U.S. Cl. .................. 510/161; 510/421; 510/424; 510/505; 510/506
(58) Field of Classification Search .................. None
See application file for complete search history.

(56) References Cited

U.S. PATENT DOCUMENTS

| 3,914,185 A | 10/1975 | Inamorato |
| 5,147,610 A | 9/1992 | Watanabe et al. |
| 5,965,512 A | 10/1999 | Smyth et al. |
| 6,063,744 A | 5/2000 | McQuillen |
| 2005/0129576 A1 | 6/2005 | Oonuma |

FOREIGN PATENT DOCUMENTS

| CN | 1566304 A | 1/2005 |
| EP | 1 253 187 A2 | 10/2002 |
| JP | 7-292387 | 11/1995 |
| JP | 3001087 | 11/1999 |
| JP | 2000-249705 | 9/2000 |
| JP | 2002-323504 | 11/2002 |
| JP | 2003-139781 | 5/2003 |

*Primary Examiner*—Necholus Ogden, Jr.
(74) *Attorney, Agent, or Firm*—Oblon, Spivak, McClelland, Maier & Neustadt, L.L.P.

(57) ABSTRACT

An alkaline detergent for an automatic analyzer is disclosed, which is consisted of an alkaline solution containing polyoxyalkylene alkylether as a nonionic surfactant, and a cloud point-adjusting organic solvent.

20 Claims, 4 Drawing Sheets

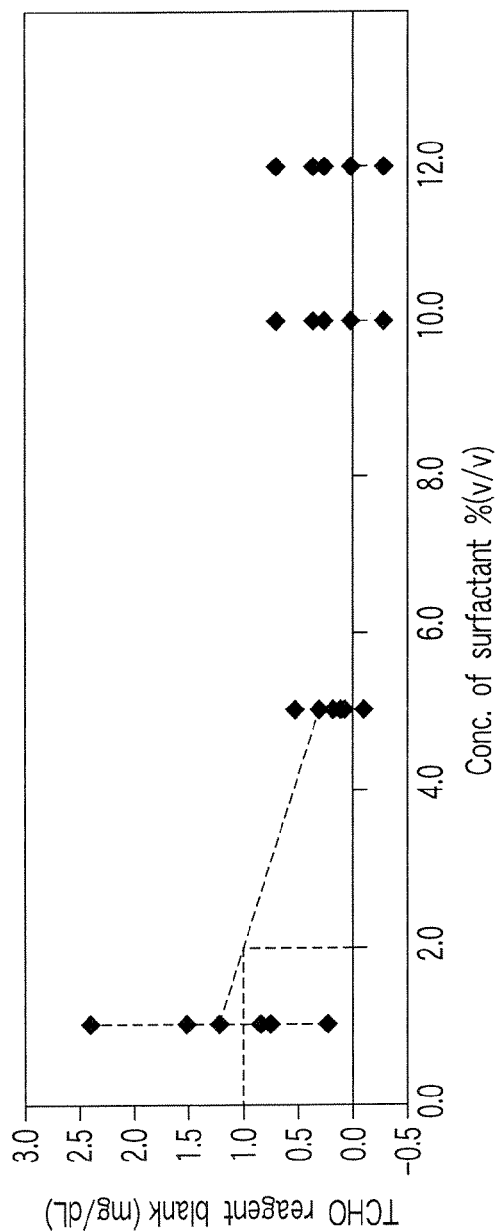
F I G. 5
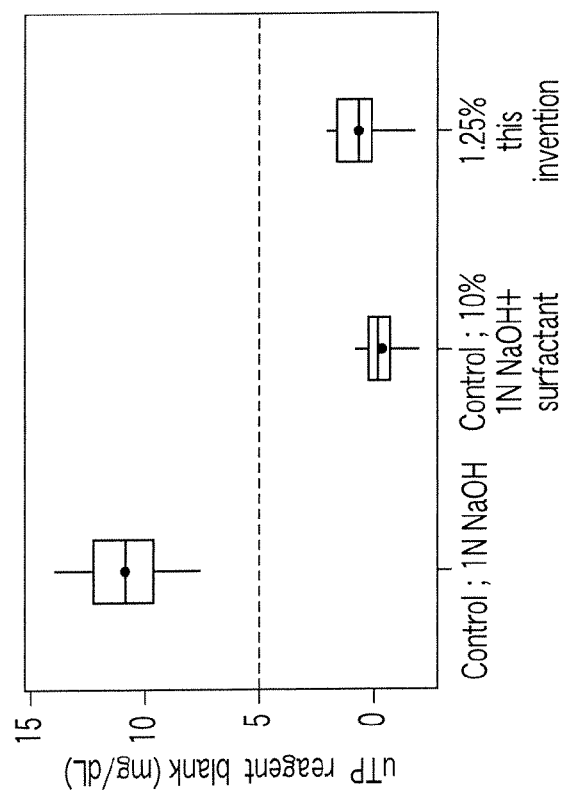
F I G. 6

ALKALINE DETERGENT FOR AUTOMATIC ANALYZER, WASHING METHOD FOR AUTOMATIC ANALYZER, AND AUTOMATIC ANALYZER

CROSS-REFERENCE TO RELATED APPLICATIONS

This application is based upon and claims the benefit of priority from prior Japanese Patent Application No. 2005-183458, filed Jun. 23, 2005, the entire contents of which are incorporated herein by reference.

BACKGROUND OF THE INVENTION

1. Field of the Invention

This invention relates to an alkaline detergent for an automatic analyzer, to a cleaning method for the automatic analyzer, and to the automatic analyzer.

2. Description of the Related Art

To clean the reaction tube to which a reaction solution of sample and reagent contacts in an automatic analyzer, there has been proposed the employment of a cleaning solution comprising an alkaline solution containing a nonionic surfactant for enhancing the detergency thereof. It has been proposed in this case to employ polyoxyethylene alkylether which is excellent in detergency as a nonionic surfactant. It has also been proposed to employ a mixture of plural kinds of polyoxyethylene alkylether differing in number of moles of oxyethylene included therein.

A cleaning solution of this kind has a cloud point (a temperature inducing whitening of the cleaning solution as the temperature of cleaning solution is increased) representing one of the properties of the surfactant, thereby occasionally raising the problem that the cleaning solution may be whitened and segregated due to the heat generated in the automatic analyzer. Meanwhile, there has been proposed a cleaning solution which regulates the cloud point of cleaning solution to a predetermined range so as to secure a sufficient detergency. In this case, since the cloud point is confined to the vicinity of working temperature, it is assumed that the cleaning solution is whitened and rendered non-uniform under the working condition. Further, there has been also proposed to employ a cleaning solution which is diluted using an organic solvent to enhance the detergency thereof without damaging to the reaction cell.

Generally speaking, a detergent containing a surfactant is whitened at the cloud point thereof. This cloud point is known to vary depending on the alkalinity of the solution, the kind of surfactant and the concentration of surfactant. However, in order to increase the alkalinity of the solution so as to enhance the detergency to smears of proteinic residue, it has been considered inevitable to regulate the concentration of surfactant to a lower level. An alkaline detergent is usually diluted with pure water on the occasion of using it in an automatic analyzer. In order to secure the content of a surfactant at a predetermined level of concentration after this dilution, the dilution magnification is controlled to a lower level. Namely, the alkaline cleaning solution usually n comprises the alkaline detergent at a concentration of as high as about 10% by volume. As the throughput capacity of the analyzer is increased, the quantity of cleaning solution to be employed also increases, thus increasing the frequency of exchanging the detergent.

Although it may be possible to avoid this increase in frequency of exchanging the detergent by using a larger detergent vessel, a detergent vessel having such a large capacity is very difficult to handle. Moreover, as the detergent vessel is increased in capacity, the space occupied by the detergent vessel in the automatic analyzer is also increased, thus leading to an increase in scale of the analyzer.

BRIEF SUMMARY OF THE INVENTION

An object of the present invention is to provide an alkaline detergent which is capable of suppressing the lowering of the cloud point of the detergent that occurs as a surfactant is incorporated into an alkaline solution and also capable of exhibiting high detergency. Another object of the present invention is to provide a cleaning method of an automatic analyzer where such an alkaline detergent is employed. A further object of the present invention is to provide an automatic analyzer which does not necessitate the enlargement of cleaning section.

According to a first aspect of the present invention, there is provided an alkaline detergent for an automatic analyzer consisting of an alkaline solution containing polyoxyalkylene alkylether as a nonionic surfactant, and a cloud point-adjusting organic solvent.

According to a second aspect of the present invention, there is provided a method of cleaning an automatic analyzer, which analyzer comprises a sampler for storing a test specimen; a reagent reservoir for holding a reagent bottle storing a reagent; a reaction disc for holding a reaction tube; a mechanism for dispensing the test specimen and the reagent into the reaction tube; a measurement section for measuring a reaction solution of the test specimen with the reagent; and a cleaning section for cleaning the reaction tube; the method comprising cleaning the reaction tube with an aqueous alkaline cleaning solution, an aqueous acidic cleaning solution and pure water, the aqueous alkaline cleaning solution comprising the alkaline detergent as claimed in claim 1 at a concentration of 1 to 3% by volume.

According to a third aspect of the present invention, there is provided an automatic analyzer comprising a sampler for storing a test specimen; a reagent reservoir for holding a reagent bottle storing a reagent; a reaction disc for holding a reaction tube; a mechanism for dispensing the test specimen and the reagent into the reaction tube; a measurement section for measuring a reaction solution of the test specimen with the reagent; and a cleaning section for cleaning the reaction tube using an aqueous alkaline cleaning solution, an aqueous acidic cleaning solution and pure water; wherein the aqueous alkaline cleaning solution contains the alkaline detergent of claim 1 at a concentration of 1 to 3% by volume.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a graph illustrating the relationship between the concentration of surfactant and the detergency; and FIG. 6 is a graph illustrating the effect of cleaning on smears of proteinic residue.

DETAILED DESCRIPTION OF THE INVENTION

Figure 1:
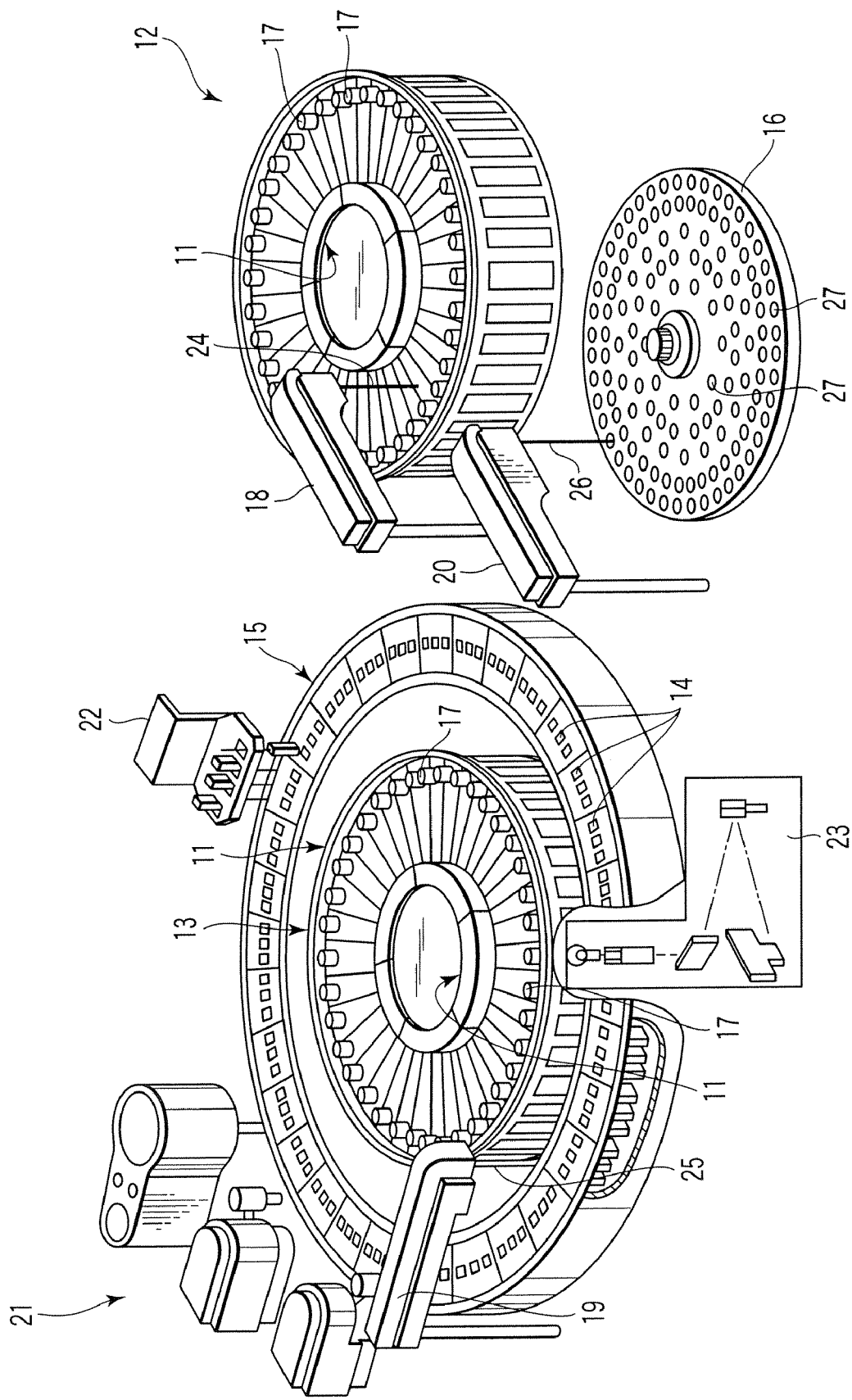
FIG. 1 is a perspective view illustrating, generally, an automatic analyzer wherein an alkaline detergent according to one embodiment of the present invention is employed.

Next, embodiments of the present invention will be explained.

The alkaline detergent for an automatic analyzer according to one embodiment of the present invention is formed of an alkaline solution containing polyoxyalkylene alkylether as a nonionic surfactant and a cloud point-adjusting organic solvent. The present inventors have taken notice of polyoxyalkylene alkylether which exhibits almost the same degree of detergency as polyoxyethylene alkylether among various nonionic surfactants. More specifically, the present inventors have taken notice of the polyoxyalkylene alkylether containing two kinds of alkylene moieties differing in number of carbon atoms included therein. Moreover, this polyoxyalkylene alkylether has a high cloud point, i.e. as high as about 80° C.

As for examples of the polyoxyalkylene alkylether, it is possible to employ, for example, the compounds represented by the following general formula (1).

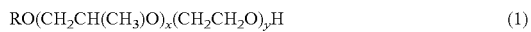

$$RO(CH_2CH(CH_3)O)_x(CH_2CH_2O)_yH \quad (1)$$

In the above general formula (1), R is alkyl group having 3 to 20 carbon atoms, preferably alkyl group having 12 carbon atoms; x and y are values representing the polymerization degree of the oxypropylene moiety and of the oxyethylene moiety, respectively. This polyoxyalkylene alkylether is available on the market by the trade name of EMULGEN LS-114 (Kao Co., Ltd.). It is also possible to employ EMULGEN LS-106, EMULGEN LS-110 and EMULGEN MS-110 (all from Kao Co., Ltd.).

It is preferable to employ polyoxyalkylene alkylether at a concentration ranging from 2% (v/v) to 10% (v/v). If the concentration of polyoxyalkylene alkylether is less than 2% (v/v), it would become difficult to obtain a sufficient effect thereof. On the other hand, even if the concentration of polyoxyalkylene alkylether is increased to exceed 10% (v/v), it would be impossible to expect any further prominent cleaning effects. It is more preferable to confine the concentration of polyoxyalkylene alkylether within the range of 3% (v/v) to 6% (v/v).

Generally speaking, the cloud point of nonionic surfactant decreases as the alkalinity is increased. It has been found out by the present inventors that it is possible, through the addition of a specific kind of organic solvent, to suppress the lowering of cloud point of polyoxyalkylene alkylether. Therefore, a cloud point-adjusting organic solvent is incorporated into the alkaline detergent according to the embodiment of the present invention.

As for the cloud point-adjusting organic solvent, it is possible to employ primary alcohol having 1 to 3 carbon atoms and secondary alcohol having 1 to 3 carbon atoms. More specifically, it is possible to employ, as a cloud point-adjusting organic solvent, methanol, ethanol, isopropanol, etc.

Among them, it is most preferable to employ ethanol because of the fact that ethanol is most effective in suppressing the lowering of cloud point.

It is preferable to employ the cloud point-adjusting organic solvent at a concentration ranging from 1% (v/v) to 10% (v/v). If the concentration of cloud point-adjusting organic solvent is less than 1% (v/v), it would become difficult to obtain a sufficient effect thereof. On the other hand, even if the concentration of cloud point-adjusting organic solvent is increased to exceed 10% (v/v), it would be impossible to expect any further enhancement of the effect of suppressing the lowering of cloud point. It is more preferable to confine the concentration of the cloud point-adjusting organic solvent within the range of 2% (v/v) to 8% (v/v).

The alkaline detergent according to one embodiment of the present invention can be prepared by dissolving the polyoxyalkylene alkylether and the cloud point-adjusting organic solvent mentioned above in an alkaline solution.

As for examples of the alkaline solution, it is possible to employ an aqueous solution of sodium hydroxide or potassium hydroxide. This alkaline solution is effective for the removal of smears of proteinic residue and inorganic residue through the dissolution and decomposition of these smears. Further, the alkaline solution is excellent in defatting and in detergency, so that the alkaline solution is effective for the removal of smears of proteinic organic matters and of lipid. Moreover, the alkaline solution is not only effective in dissolving and decomposing these smears but also effective in enhancing the solubility of protein included in blood serum, etc. The test specimen (blood and urine) to be handled by an automatic analyzer contains protein and lipid. Further, the reagent also tends to contain a large quantity of proteinic components such as enzyme, etc.

The alkaline detergent is diluted with pure water so as to make it an aqueous solution of alkaline detergent on the occasion of using it for an automatic analyzer. In order to sufficiently secure the effect of alkaline detergent to enhance the solubility of smears and protein, the pH of aqueous solution of alkaline detergent after the dilution should preferably be 11 or more. Therefore, the pH of alkaline detergent should be determined taking the dilution magnification thereof into consideration so as to obtain a pH value falling within a predetermined range after the dilution thereof.

Sodium hypochlorite and/or sodium carbonate may be incorporated, as an additive, into the alkaline detergent according to one embodiment of the present invention. Sodium hypochlorite is effective in enhancing the solubilizing reactivity of smear component. Sodium carbonate is effective, as an auxiliary for the surfactant, in enhancing the surface activity of the surfactant. These additives may be incorporated in the alkaline detergent at a concentration ranging from 0.1 to 5 wt % in order to secure a sufficient effect of these additives.

Next, the construction of the analyzer according to one embodiment of the present invention will be explained with reference to drawings.

FIG. 1 shows a perspective view illustrating the entire structure of the automatic analyzer according to one embodiment of the present invention. This automatic analyzer comprises reagent reservoir 12 and 13 designed to mount a reagent rack 11 for housing a plurality of reagent bottles each containing a reagent capable of reacting with a specific component of test specimen, a reaction disc 15 in which a plurality of reaction tubes 14 can be arranged along the peripheral thereof, and a disc sampler 16 in which test specimen vessels 27 each containing a test specimen can be set thereon.

The reagent reservoir 12 and 13, the reaction disc 15 and the disc sampler 16 are all rotate by a driving device. A reagent required for measurement is dispensed from a reagent bottle 17 stored in the reagent rack 11 of the reagent reservoir 12 or 13 to each one of the reaction tubes 14 disposed on the reaction disc 15 by using a dispensing arm 18 or 19.

Further, a test specimen stored in one of the test specimen vessels 27 disposed on the disc sampler 16 is dispensed to the reaction tube 14 disposed on the reaction disc 15 by a sampling probe 26 of a sampling arm 20. The reaction tube 14 having a test specimen and a reagent dispensed therein is then moved to an agitating section through the rotation of the reaction disc 15. At this agitating section, the test specimen and the reagent are agitated and mixed together by an agitating unit 21, thereby creating a mixed solution (reaction solution). Subsequently, by a photometry system 23, light is irradiated to the reaction tube 14 that has been moved to the photometric position, thereby measuring changes in absorbency of the reaction solution placed in the reaction tube 14, thus performing the analysis of components of the test specimen. Upon finishing the analysis, the reaction solution in the reaction tube 14 is discarded and then the reaction tube 14 is cleaned by a cleaning unit 22.

Figure 2:
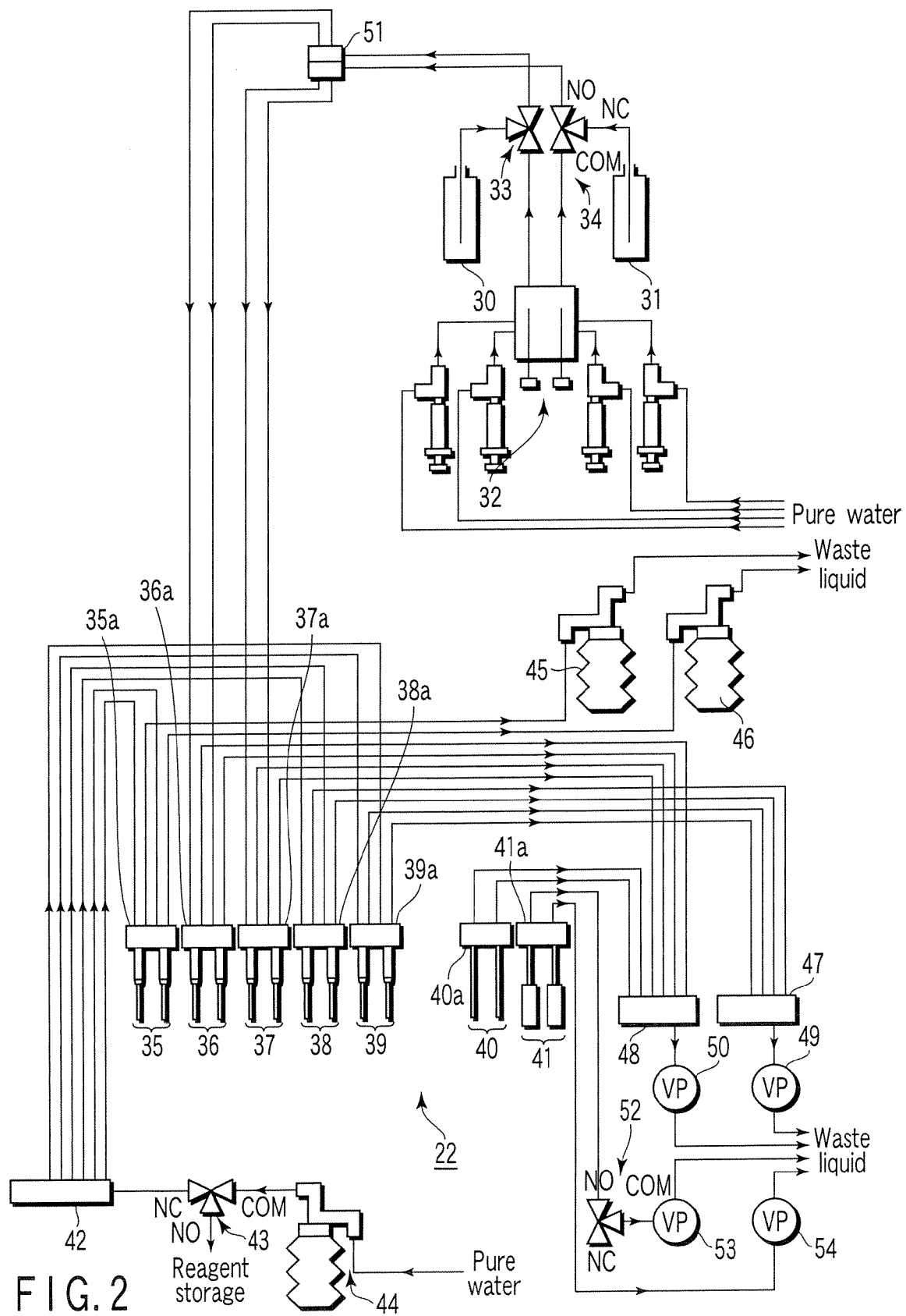
FIG. 2 is a block diagram illustrating a cleaning system in an automatic analyzer according to one embodiment of the present invention.

Next, the details of the cleaning unit 22 will be explained. FIG. 2 is a block diagram illustrating a cleaning system including the cleaning unit 22 in the automatic analyzer. In FIG. 2, this cleaning system of the automatic analyzer comprises an alkaline detergent bottle 30 storing an alkaline detergent stock solution, an acidic detergent bottle 31 storing an acidic detergent stock solution, and a detergent pump 32 which mixes the alkaline detergent stock solution placed in the alkaline detergent bottle 30 with pure water so as to form an aqueous solution of alkaline detergent and also mixes the acidic detergent stock solution placed in the acidic detergent bottle 31 with pure water so as to form an aqueous solution of acidic detergent.

This cleaning system also comprises electromagnetic valves 33 and 34 for controlling the flows of the aqueous solution of alkaline detergent and of the aqueous solution of acidic detergent, which are created, through the supply of electric power to a controlling section (not shown), from the alkaline detergent stock solution, the acidic detergent stock solution using the detergent pump 32. Incidentally, the symbols "NO" (normal open) attached to each of these electromagnetic valves 33 and 34 in FIG. 2 indicates that these electromagnetic valves are brought into the open state thereof at the moment when there is no supply of electric power and can be brought into the closed state when electric power is supplied thereto. The symbols "NC" (normal close) attached thereto likewise indicates that these electromagnetic valves are brought into the close state thereof at the moment when there is no supply of electric power and can be brought into the open state when electric power is supplied thereto. Further, the symbols of "COM" (common hole) attached thereto likewise indicates that these electromagnetic valves are common valves.

The cleaning unit 22 is constituted by a first cleaning nozzle unit 35 for executing the delivery and suction of high concentration waste liquid with respect to the reaction tube 14, by a second cleaning nozzle unit 36 for executing the delivery and suction of aqueous solution of alkaline detergent with respect to the reaction tube 14, by a third cleaning nozzle unit 37 for executing the delivery and suction of aqueous solution of acidic detergent with respect to the reaction tube 14, by a fourth cleaning nozzle unit 38 for executing the delivery and suction of pure water with respect to the reaction tube 14, by a fifth cleaning nozzle unit 39 for executing the delivery and suction of pure water with respect to the reaction tube 14, a suction nozzle unit 40 for executing the suction of residual water left in the reaction tube, and by a drying nozzle unit 41 for drying the interior of the reaction tube 14 having residual water sucked therein.

Each of nozzle units 35 to 41 are provided with elevating mechanisms 35a to 41a, respectively. The control section controls the upward and downward movement of each of nozzle units 35 to 41 through these elevating mechanisms 35a to 41a, respectively.

The first cleaning nozzle unit 35, the fourth cleaning nozzle unit 38 and the fifth cleaning nozzle unit 39 are connected, via a branch tube 42 and an electromagnetic valve 43, with a bellows pump 44 for cleaning, which feeds pure water to each of the nozzle units 35, 38 and 39.

Further, the first cleaning nozzle unit 35 is connected with bellows pumps 45 and 46 for handling a waste liquid of high concentration, so that a waste liquid of high concentration that has been delivered into the reaction tube 14 through the bellows pump 44 for cleaning can be sucked by these bellows pumps 45 and 46 for high concentration waste liquid and then discharged.

The fourth and fifth cleaning nozzle units 38 and 39 are connected, via branch tubes 47 and 48 respectively, with vacuum pumps 49 and 50 (VP), respectively. Therefore, a waste liquid of pure water that has been delivered into the reaction tube 14 through the bellows pump 44 for cleaning can be sucked by these vacuum pumps 49 and 50 and then discharged.

The second cleaning nozzle unit 36 is connected, via a branch tube 51 and an electromagnetic valve 33, with the detergent pump 32 and also connected, via a branch tube 48, with the vacuum pump 50, so that an aqueous solution of alkaline detergent that has been delivered into the reaction tube 14 through the detergent pump 32 can be sucked by the vacuum pump 50 and then discharged.

Likewise, the third cleaning nozzle unit 37 is connected, via a branch tube 51 and an electromagnetic valve 34, with the detergent pump 32 and also connected, via a branch tube 48, with the vacuum pump 50, so that an aqueous solution of acidic detergent that has been delivered into the reaction tube 14 through the detergent pump 32 can be sucked by the vacuum pump 50 and then discharged.

The suction nozzle 40 is connected, via the branch tube 48, with the vacuum pump 50, so that residual water left in the reaction tube 14 can be sucked by this vacuum pump 50 and then discharged.

The drying nozzle unit 41 is connected, via an electromagnetic valve 52, with the vacuum pump 53 and also connected with the vacuum pump 54, thereby enabling the interior of the reaction tube 14 to be dried by the vacuum pumps 53 and 54.

Each of the reaction tubes 14 is successively moved under control from the first cleaning nozzle unit 35 to the drying nozzle unit 41. As a result, these reaction tubes 14 are successively subjected to a series of procedures including, mentioning in order, "suction of a high concentration waste liquid"→"delivery/suction of pure water"→"delivery of an aqueous solution of alkaline detergent"→"suction of an aqueous solution of alkaline detergent"→"delivery of an aqueous solution of acidic detergent"→"suction of an aqueous solution of acidic detergent"→"a first delivery of pure water"→"a first suction of pure water"→"a second delivery of pure water"→"a second suction of pure water"→"suction of residual water"→"drying".

An alkaline detergent bottle 30 stores the aforementioned alkaline detergent according to one embodiment of the present invention and then diluted with pure water to obtain an aqueous solution of alkaline detergent having a concentration of 1 to 3% by volume. The cleaning of the reaction tube 14 is performed using this aqueous solution of alkaline detergent. As already explained above, the alkaline detergent according to one embodiment of the present invention may contain, as a nonionic surfactant, polyoxyalkylene alkylether at a concentration ranging from 2% (v/v) to 10% (v/v). Since this nonionic surfactant is enabled to be included in the alkaline detergent at such a high concentration, the alkaline detergent is enabled to be diluted to create an aqueous solution thereof having such a low concentration of as low as 1 to 3% by volume on the occasion of using it for cleaning the reaction tube. If the concentration of the alkaline detergent is less than 1% by volume, it may become difficult to secure a sufficient detergency. On the other hand, if the concentration of the alkaline detergent exceeds 3% by volume, the frequency of exchanging the detergent may be increased, thereby necessitating the employment of a larger detergent vessel in order to limit the frequency of detergent exchange to almost the same as that of the prior art. The alkaline detergent according to one embodiment of the present invention is capable of enhancing the throughput without necessitating the employment of a larger detergent vessel and also capable of securing sufficiently high detergency.

Furthermore, the alkaline detergent according to one embodiment of the present invention is capable of obviating the generation of whitening or segregation even under the working condition of apparatus, so that it is not required to preserve the alkaline solution in a separate container from the container for the surfactant. If it is required to separately preserve the alkaline detergent in a container, it would lead to increased complication in structure of the cleaning system of automatic analyzer. According to the present invention, such a trouble can also be obviated.

Next, the present invention will be explained with reference to specific examples.

EXAMPLE 1

4% (v/v) of polyoxyalkylene alkylether (EMULGEN LS-114; Kao Co., Ltd.) was added, as a nonionic surfactant, to a 1.2N aqueous solution of sodium hydroxide employed as an alkaline solution to obtain a mixed solution, to which ethanol was added as a cloud point-adjusting organic solvent to prepare an alkaline detergent. In this case, the concentration of ethanol was variously modified to obtain various alkaline detergents each having 2%, 4%, 6%, 8% or 10% (v/v) in ethanol concentration. Then, the cloud point of each of these alkaline detergents thus obtained was measured. Incidentally, the cloud point, measured as a simple substance, of polyoxyalkylene alkylether employed as a nonionic surfactant (3% (v/v) in concentration) was 88° C.

Figure 3:
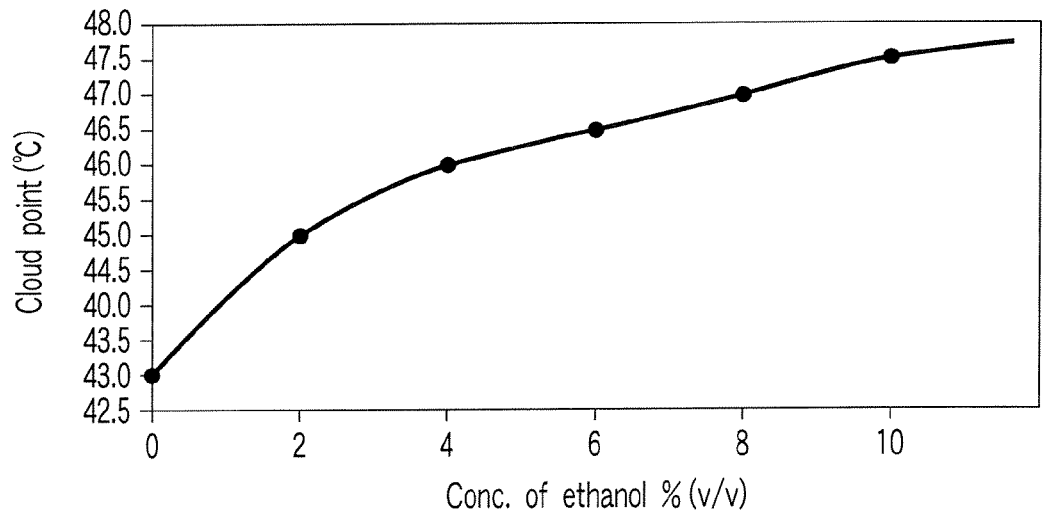
FIG. 3 is a graph illustrating the relationship between the concentration of ethanol and the cloud point.

The relationship between the concentration and the cloud point is illustrated in FIG. 3. For the purpose of comparison, the cloud point of the detergent which was prepared according to the same procedures as described above except that ethanol was not incorporated therein is also shown in FIG. 3.

As shown in FIG. 3, the cloud point of detergent in the case where ethanol was not incorporated therein, i.e., of the detergent in a 1.2N NaOH solution, was 43° C. By contrast, as the concentration of ethanol was increased, the cloud point of the detergent was increased. However, there was a limitation with regard to the increase of cloud point, so that as the concentration of ethanol was increased up to about 10% (v/v), the cloud point became almost constant.

EXAMPLE 2

4% (v/v) of a nonionic surfactant, 0.2% of sodium carbonate and 10% (v/v) of ethanol as a cloud point-adjusting organic solvent were added to a 1.2N aqueous solution of sodium hydroxide employed as an alkaline solution to obtain an alkaline detergent. In this case, as the nonionic surfactant, polyethylene glycol, polyoxyethylene laurylether, polyoxyethylene propyleneglycol and polyoxyalkylene alkylether were respectively employed.

By using the automatic analyzer as shown in FIG. 1, the cleaning of smear of pseudo-lipid was performed to compare the detergency of each of alkaline detergents. First of all, a reaction solution comprising a mixture of serum and a GOT-measuring reagent was poured into a reaction tube and heated at a constant temperature of 40° C. for one hour to create smear of pseudo-lipid. The concentration of the alkaline detergent used was set to 1.25% by volume to perform the cleaning of the reaction tube. Then, the reagent blank of T-CHO was measured.

Figure 4:
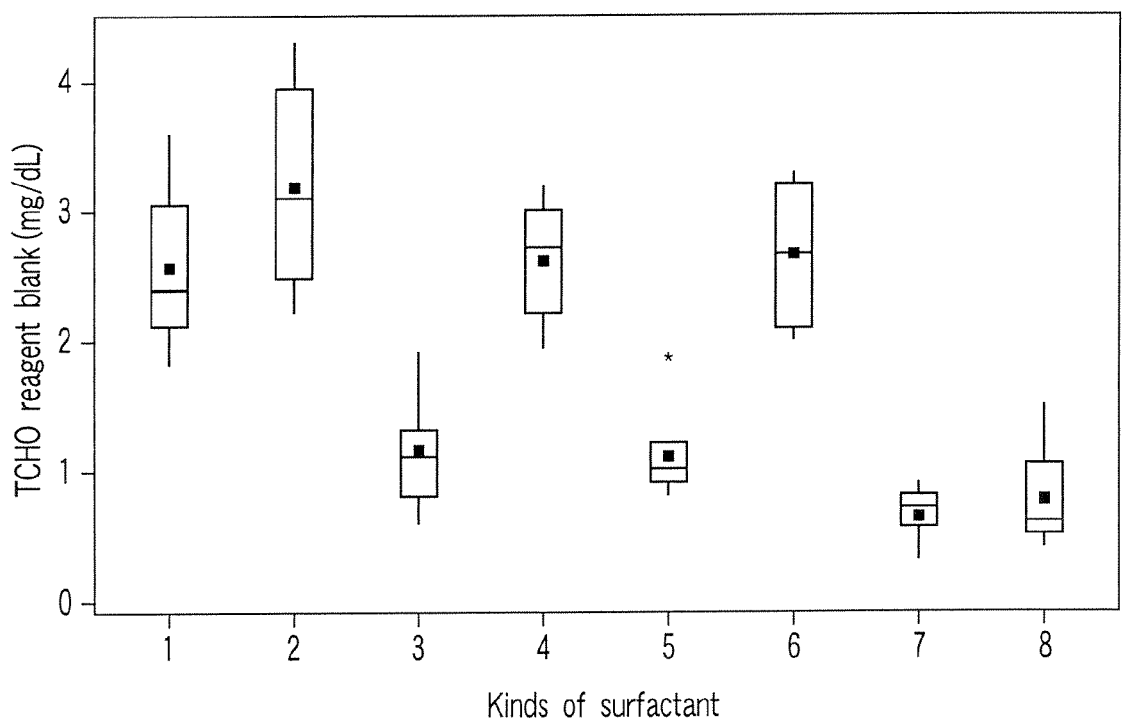
FIG. 4 is a graph illustrating the comparison of detergency according to the kinds of surfactants.

The detergency of each of the cleaning solutions thus obtained was summarized in FIG. 4. Incidentally, the surfactants 1 to 8 shown in FIG. 4 were as follows.

1: Polyethylene glycol (Toho Polyethylene Glycol 400; Toho Kagaku Kogyo Co., Ltd.)
2: Polyoxyethylene laurylether (1) (Kao EMULGEN 150; Kao Co., Ltd.)
3: Polyoxyethylene laurylether (2) (Kao EMULGEN 147; Kao Co., Ltd.)
4: Polyoxyethylene laurylether (3) (Kao EMULGEN 130; Kao Co., Ltd.)
5: Polyoxyethylene laurylether (4) (Kao EMULGEN 123P; Kao Co., Ltd.)
6: Polyoxyethylene propyleneglycol (Kao EMULGEN PP-290; Kao Co., Ltd.)
7: Polyoxyalkylene alkylether (1) (Kao EMULGEN LS-114; Kao Co., Ltd.)
8: Polyoxyalkylene alkylether (2) (Kao EMULGEN LS-110; Kao Co., Ltd.)

It was confirmed from the results shown in FIG. 4 that the alkaline detergent that contains polyoxyalkylene alkylether as a nonionic surfactant was the highest in detergency.

EXAMPLE 3

An alkaline detergent was prepared by following the same procedures as described in Example 1 except that the concentration of polyoxyalkylene alkylether employed as a nonionic surfactant was changed to 1% (v/v), 5% (v/v) and 10% (v/v).

The detergency of each of the cleaning solutions thus obtained was investigated in the same manner as described in the above-mentioned Example 2 to obtain the results shown in FIG. 5. It will be seen from FIG. 5 that as long as the concentration of the nonionic surfactant is not less than 2% (v/v), it is possible to obtain excellent detergency.

EXAMPLE 4

4% (v/v) of polyoxyalkylene alkylether employed as a nonionic surfactant, 10% (v/v) of ethanol employed as a cloud point-adjusting organic solvent, and 0.6% of sodium hypochlorite were added to a 1.2N aqueous solution of sodium hydroxide employed as an alkaline solution to prepare an alkaline detergent of this example.

By using the automatic analyzer as shown in FIG. 1, the cleaning of smears of a trace amount of proteinic residue was performed to investigate the detergency of the alkaline detergent of this example.

First of all, pool serum was employed as a sample and ion-exchange water was employed as a reagent in order to smear a reaction tube. The reaction tube thus smeared was subjected to cleaning by using an aqueous solution of alkaline detergent which was prepared by diluting the alkaline detergent of this example so as to contain the alkaline detergent at a concentration of 1.25% by volume. Subsequently, by using ion-exchange water having a concentration of 0% as a sample and also by using a reagent for measuring uTP, the uTP was measured to confirm the level of smear.

Further, by using a 1N NaOH alkaline solution containing no surfactant as a contrast, and by using a 1N NaOH alkaline detergent (10 vol. % in concentration) containing, as a surfactant, polyoxyalkylene alkylether as another contrast, the detergency of these detergents to smear of proteinic residue was investigated in the same manner as described above. This concentration of 10 vol. % corresponds to the same level of concentration of the conventional alkaline detergent in the actual use thereof.

The results thus obtained are summarized in FIG. 6. As shown in FIG. 6, while an average of the reagent blank of the 1N NaOH alkaline solution containing no surfactant was 11 mg/dL, the alkaline detergent of this example indicated 0.5 mg/dL, thus demonstrating substantial improvement of detergency.

This improvement of detergency is almost the same as the detergency that can be obtained when a 1N NaOH alkaline detergent containing a surfactant is employed at a concentration of 10 vol. %, thus finding that, even if the concentration of the alkaline detergent is lowered in actual use thereof, it is possible to obtain almost the same degree of excellent detergency as obtainable in the conventional detergent.

EXAMPLE 5

Assuming that an alkaline detergent was set in an automatic analyzer having a throughput of 800 tests/hour, the size of detergent vessel and the frequency of exchange of detergent were calculated.

For example, in order to adjust a concentration of use to 1.25% by volume, 10 μL of the alkaline detergent should be diluted with 1000 μL of ion-exchange water every time. If an alkaline detergent vessel having a capacity of 500 mL is employed, the frequency of exchanging the detergent vessel can be calculated as follows and would become about every two weeks.

500,000÷800 tests/hour÷5 hour operation/day÷10 μL/once=12.5 days

On the other hand, if a concentration of use is set to 10% by volume, 100 μL of the alkaline detergent should be diluted with 900 μL of ion-exchange water every time. If the size of detergent vessel is as small as 500 mL, the frequency of exchanging the detergent vessel would become 1.5 days, thus greatly increasing the frequency of exchange.

Because of these reasons, the detergent vessel that has been conventionally employed is 2 L size (about 240 mm×135 mm×80 mm). Whereas, when the alkaline detergent according to one embodiment of the present invention is employed, the size of the detergent vessel having a capacity of 500 mL (about 180 mm×100 mm×40 mm) can be employed. As described above, it is now possible to secure a sufficient detergency without necessitating the enlargement in scale of cleaning section.

According to the present invention, it is possible to provide an alkaline detergent which is capable of suppressing the lowering of the cloud point of the detergent that occurs as a surfactant is incorporated into an alkaline solution and also capable of exhibiting high detergency. Further, according to the present invention, it is possible to provide an automatic analyzer which does not necessitate the enlargement of cleaning section and also a cleaning method of such an automatic analyzer.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An alkaline detergent for an automatic analyzer consisting of an alkaline solution containing polyoxyalkylene alkylether as a nonionic surfactant, and a cloud point-adjusting organic solvent,
   wherein the nonionic surfactant comprises two kinds of alkylene groups differing in the number of carbon atoms.

2. The detergent according to claim 1, wherein the nonionic surfactant is incorporated at a concentration ranging from 2%(v/v) to 10%(v/v).

3. The detergent according to claim 1, wherein the nonionic surfactant comprises ethylene and propylene as alkylene moiety.

4. The detergent according to claim 1, wherein the nonionic surfactant comprises lauryl ether as alkylether moiety.

5. The detergent according to claim 1, wherein the cloud point-adjusting organic solvent is incorporated at a concentration ranging from 1%(v/v) to 10%(v/v).

6. The detergent according to claim 1, wherein the cloud point-adjusting organic solvent is selected from primary alcohol having 1 to 3 carbon atoms and secondary alcohol having 1 to 3 carbon atoms.

7. A method of cleaning an automatic analyzer, which analyzer comprises:
   a sampler for storing a test specimen;
   a reagent reservoir for holding a reagent bottle storing a reagent;
   a reaction disc for holding a reaction tube;
   a mechanism for dispensing the test specimen and the reagent into the reaction tube;
   a measurement section for measuring a reaction solution of the test specimen with the reagent; and
   a cleaning section for cleaning the reaction tube;
   the method comprising cleaning the reaction tube with an aqueous alkaline cleaning solution, an aqueous acidic cleaning solution and pure water, the aqueous alkaline cleaning solution comprising the alkaline detergent as claimed in claim 1 at a concentration of 1 to 3% by volume.

8. The cleaning method according to claim 7, wherein the alkaline cleaning solution has a pH of 11 or more.

9. The cleaning method according to claim 7, wherein the nonionic surfactant is incorporated in the alkaline detergent at a concentration ranging from 2%(v/v) to 10%(v/v).

10. The cleaning method according to claim 7, wherein the nonionic surfactant incorporated in the alkaline detergent comprises ethylene and propylene as alkylene moiety.

11. The cleaning method according to claim 7, wherein the nonionic surfactant incorporated in the alkaline detergent comprises lauryl ether as alkylether moiety.

12. The cleaning method according to claim 7, wherein the cloud point-adjusting organic solvent is incorporated in the alkaline detergent at a concentration ranging from 1%(v/v) to 10%(v/v).

13. The cleaning method according to claim 7, wherein the cloud point-adjusting organic solvent incorporated in the alkaline detergent is selected from primary alcohol having 1 to 3 carbon atoms and secondary alcohol having 1 to 3 carbon atoms.

14. An automatic analyzer comprising:
a sampler for storing a test specimen;
a reagent reservoir for holding a reagent bottle storing a reagent;
a reaction disc for holding a reaction tube;
a mechanism for dispensing the test specimen and the reagent into the reaction tube;
a measurement section for measuring a reaction solution of the test specimen with the reagent; and
a cleaning section for cleaning the reaction tube using an aqueous alkaline cleaning solution, an aqueous acidic cleaning solution and pure water;
wherein the aqueous alkaline cleaning solution contains the alkaline detergent of claim 1 at a concentration of 1 to 3% by volume.

15. The analyzer according to claim 14, wherein the alkaline cleaning solution has a pH of 11 or more.

16. The analyzer according to claim 14, wherein the nonionic surfactant incorporated in the alkaline detergent comprises ethylene and propylene as alkylene moiety.

17. The analyzer according to claim 14, wherein the nonionic surfactant incorporated in the alkaline detergent comprises lauryl ether as alkylether moiety.

18. The analyzer according to claim 14, wherein the cloud point-adjusting organic solvent incorporated in the alkaline detergent is selected from primary alcohol having 1 to 3 carbon atoms and secondary alcohol having 1 to 3 carbon atoms.

19. The method of claim 7, wherein the aqueous alkaline cleaning solution consists of the alkaline detergent.

20. The analyzer according to claim 14, wherein the aqueous alkaline cleaning solution consists of the alkaline detergent.

* * * * *